United States Patent [19]

Oobayashi

[11] Patent Number: Plant 6,386

[45] Date of Patent: Nov. 8, 1988

[54] SPATHIPHYLLUM PLANT

[75] Inventor: Hideo Oobayashi, Toyohashi, Japan

[73] Assignee: Yugen Kaisha Daijuen, Toyohashi, Japan

[21] Appl. No.: 859,080

[22] Filed: May 2, 1986

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—Kenyon & Kenyon

[57] ABSTRACT

A new and distinct plant variety of the Spathiphyllum which has larger ratio of bract to the whole plant as well as of bract to leaf in length, dark green colored leaves and round, big, erect and yellowish white colored bracts.

4 Drawing Sheets

DISCOVERY

The present invention relates to a new and distinct variety of ornamental plant of the genus *Spathiphyllum clevelandii* var Tasson, which has been named *Spathiphyllum clevelandii* var Merry by the inventor.

The new variety was discovered in the summer of 1982 in the Daiju-En Nursery located at 61-2 Motomachi, Minamiohshimizucho, Toyohashi-shi, Aichi-ken, Japan.

REPRODUCTION

The new variety has been asexually reproduced at the same location by applying, firstly, means of tissue culture for 6 months, secondly, means of acclimation for 1 month and, finally, means of cultivation from 1 year to 2 years, and has been found to retain its distinctive characteristic through successive asexual reproduction.

CHARACTERISTICS

The new plant variety is visually distinguished by the following characteristics of the leaf, including an elliptic form with sagitate base and cuspidate leaf tip, and bract the minimum length of which is half of the whole length of the leaf. The leaf and bract include pinnate veins, having smooth midribs and depressed veins. The new plant variety grows very densely and compactly and has medium long, wide, elliptically shaped, densely spreading leaves.

As contrasted with mother plant, the new plant variety has a large ratio of bract to the whole plant as well as of bract to leaf in length than those of mother plant.

The accompanying drawings serve by color photographic as means to illustrate typical plant of the new variety in approximately its true colors, the plant shown being approximately 31 months old, at the time of photographing, from the initiation of reproduction by tissue culture. The specimen was at that time 31 5/16 inches (about 79.5 cm) tall from the ground to the tip of the central bract.

However, the illustration of the plant in the drawing are affected by reflected ray from surface of those leaves which are highlighted.

Thus the color references are in fact made to leaves or portion of leaves which are in the shadow. There exists one or more petals in the new variety. The petal is also called perianth segment, botanically, because it is not possible to distinguish the petal from the calyx due to their copulation with each other. There also exists a bud before flowering, i.e., the perianth segment opens.

In the following detailed description of the new plant variety, the color method chosen for identification has been taken of the Japan Color Standard for Horticultural Plants.

DETAILED PLANT DESCRIPTION

Figure 1:
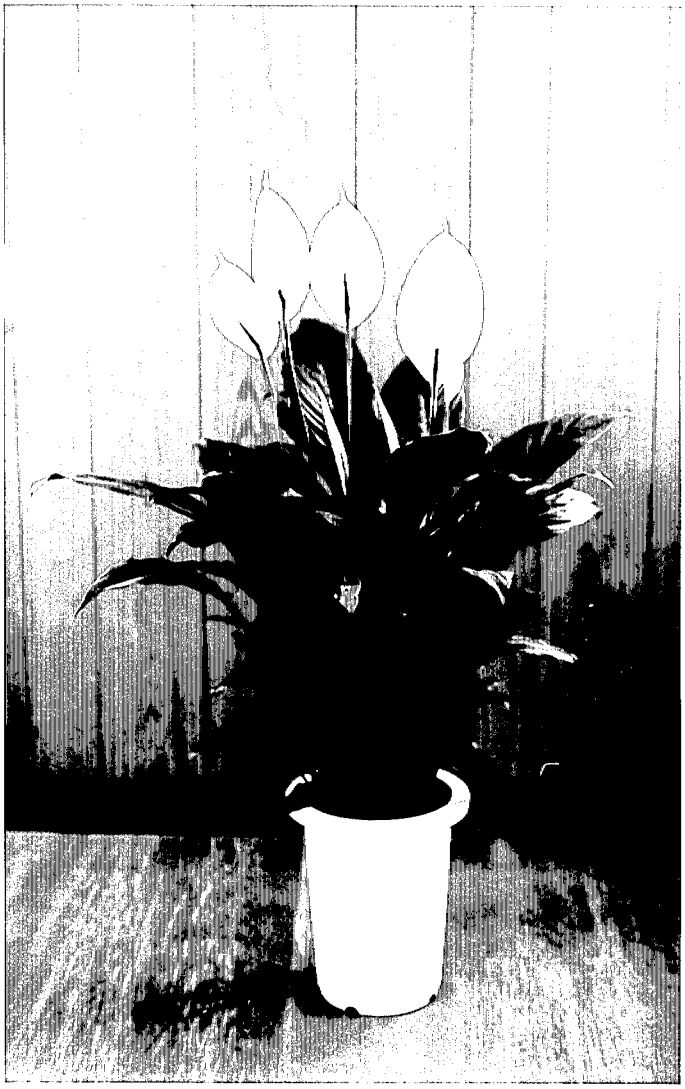
FIG. 1 is a photograph of potted plant of a new variety, *Spathiphyllum clevelandii* var. Merry. The plant shown in FIG. 1, is grown from one young plant reproduced by means of tissue culture, and approximately 31 months old, at the time of photographing, from the initiation of reproduction by tissue culture. This photograph shows that the new variety has a larger ratio of bract to the whole plant in length i.e. approximately 23% and ratio of bract to the leaf in length i.e. 74% than those of the mother plant, *Spathiphyllum clevelandii* var. Tasson which has such two ratios of approximately 18% and 44% respectively.
Figure 2:
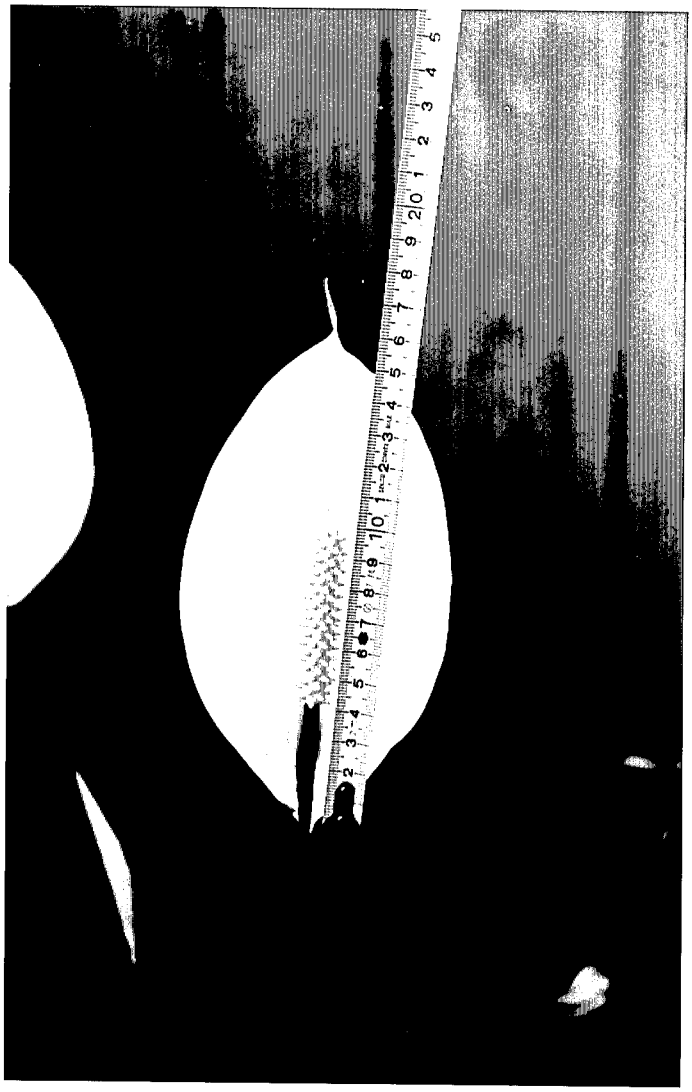
FIG. 2 is a photograph of bract and spadix with a tape measure. It is possible to see approximate length of bract (18 cm) and spadix (6 cm). The plant is approximately 31 months old from the initiation of reproduction by tissue culture.
Figure 3:
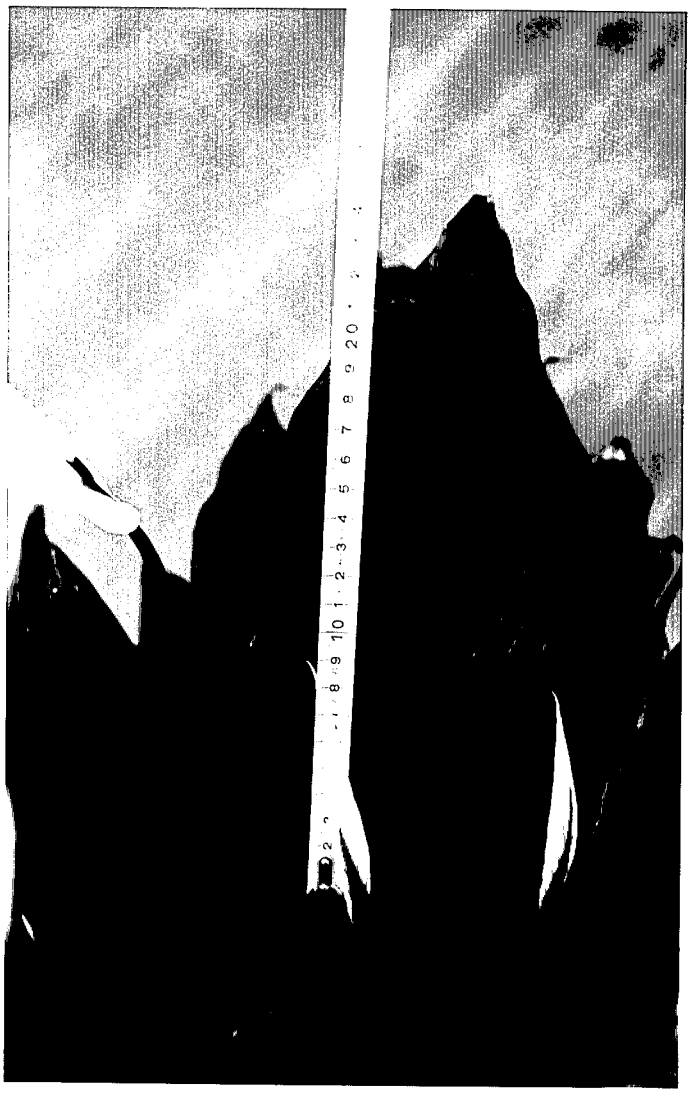
FIG. 3 is a photograph of leaf blade with a tape measure. It is possible to see approximate length of leaf brade (25 cm). The plant is approximately 31 months old from the initiation of reproduction by tissue culture.
Figure 4:
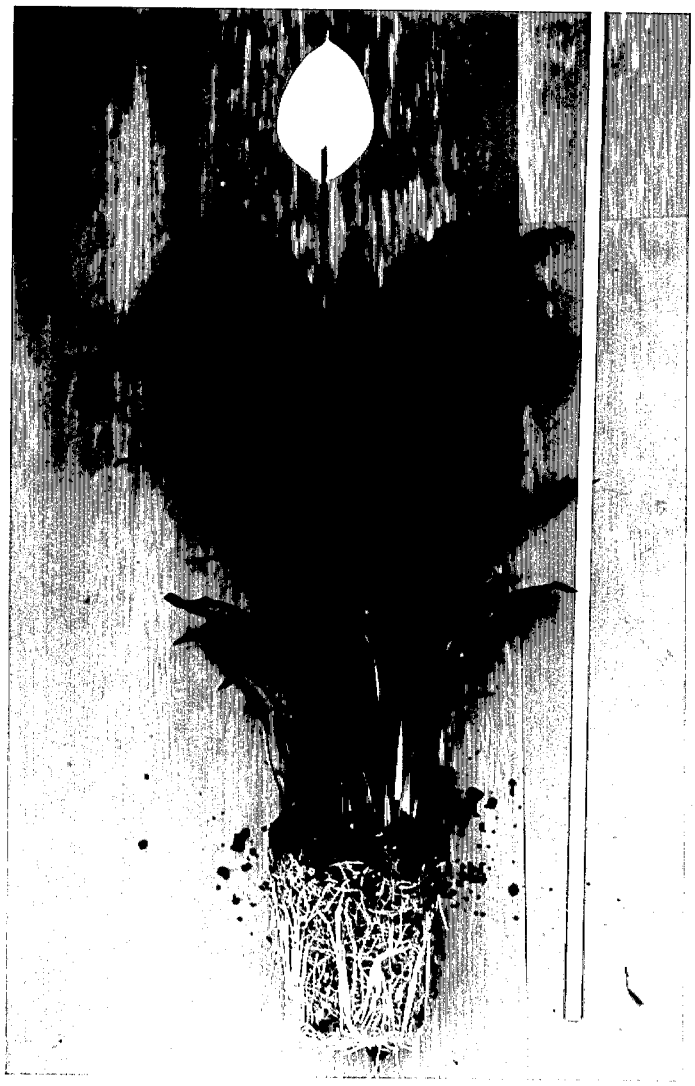
FIG. 4 is a photograph of whole part of the new variety. It is possible to see how vigorous its roots are. The plant shown is also grown from one young plant reproduced by means of tissue culture, and approximately 31 months old from the initiation of reproduction by tissue culture.

Name of the new plant variety: "*Spathiphyllum clevelandii* var Merry".

Feature of the new plant variety being cultivated about 2 years after potting.

Form: Herbaceous.

Growth: Vigorous.

Overall size: Expected size to be approximately 31⅛ inches (79 cm) in height, from ground to tip of bract or leaf blade.

Leaf Blade

Quantity: Normal.

Shape: Lanceolate.

Texture (Upper side): Glossy.
Ribs and veins: Ordinary.
Edge: Smooth.
Length: From tip of leaf to base of leaf varying from 8 1/16 inches (about 20.5 cm) to 11⅝ inches (about 29.5 cm).
Width: At widest point, from 3 9/16 inches (about 9.0 cm) to 4¾ inches (about 12.0 cm).
Color characteristic: Dark green (plate No. 7GY/3707 of the Japan Color Standard for Horticultural Plants).

Bract

Fragrance: Moderate.
Length: From tip of bract to base of bract varying from 6 5/16 inches (about 16.0 cm) to 8¼ inches (about 21.0 cm).
Width: At widest point, from 3 5/16 inches (about 8.5 cm) to 4⅛ inches (about 10.5 cm).
Color characteristic: Yellowish White (plate No. 3GY/3302 of the Japan Color Standard for Horticultural Plants).
No bract in October and November in Japan.

Spadix

Variety: Fertile.
Aspect: Smooth.
Length: From tip of spadix to base of spadix varying from 1 15/16 inches (about 5.0 cm) to 2¾ inches (about 7.0 cm).
Width: At widest point, from ⅜ inches (about 1.0 cm) to 13/16 inches (about 2.0 cm).
Color characteristic: Pale yellow (plate No. 5Y/2503 of the Japan Color Standard for Horticultural Plants).
Color at maturity: Green.
Feature of the new plant variety being cultivated about 1 year after potting.
Form: Herbaceous.
Growth: Vigorous.

Leaf blade

Quantity: Normal.
Shape: Lanceolate.
Texture (Upper side): Glossy.
Ribs and veins: Ordinary.
Edge: Smooth.
Length: From tip of leaf to base of leaf sheath varying from 6 11/16 inches (about 17.0 cm) to 9 7/16 inches (about 24.0 cm).
Width: At widest point, from 2 3/16 inches (about 5.5 cm) to 3⅜ inches (about 8.5 cm).
Color characteristic: Dark green (plate No. 7GY/3707 of the Japan Color Standard for Horticultural Plants).

Bract

Fragrance: Moderate.
Length: From tip of bract to base of bract varying from 3 15/16 inches (about 10.0 cm) to 5/162 inches (about 15.0 cm).
Width: At widest point, from 2 9/16 inches (about 6.5 cm to 3⅜ inches (about 8.5 cm).
Color characteristic: Yellowish white (plate No. 3GY/3302 of the Japan Color Standard for Horticultural Plants).
No bract in October and November in Japan.

Spadix

Variety: Fertile.
Aspect: Smooth.
Length: From tip of spadix to base of spadix varying from 1 9/16 inches (about 4.0 cm) to 2⅜ inches (about 6.0 cm).
Width: At widest point, from ⅜ inches (about 1.0 cm) to 13/16 inches (about 2.0 cm).

COMPARISON DATA

| | | BOTANICAL CLASSIFICATION | |
|---|---|---|---|
| | | NEW VARIETY *Spathiphyllum Clevelandii* var Merry | NEAREST OLD VARIETY *Spathiphyllum Clevelandii* var Tasson |
| Size of Bract | length | 7 5/16 inches<br>18.5 cm | 5½ inches<br>14.0 cm |
| | width | 3¾ inches<br>9.5 cm | 2¾ inches<br>7.0 cm |
| Length of Spadix | | 2⅜ inches<br>6.0 cm | 3⅜ inches<br>8.5 cm |
| Size of Leaf | length | 9⅞ inches<br>25.0 cm | 12⅝ inches<br>32.0 cm |
| | width | 4⅛ inches<br>10.5 cm | 5⅛ inches<br>13.0 cm |
| Height of plant, depending on culture | | 31 5/16 inches<br>79.5 cm | 30 5/16 inches<br>77.0 cm |

As compared with the nearest old variety, *Spathiphyllum clevelandii* var Tasson, the new variety has features as follows:

1. Bract:
   (a) *Shape.*—Rounder and bigger.
   (b): *Color.*—Whiter.
   (c) *Bract stalk.*—Thicker and erecter.
   (d) *Number of bract.*—More.
   (e) *Thickness.*—Thicker.
2. Foliage:
   (a) *Color.*—Darker.
   (b) *Leaf thickness.*—Thicker and erecter.

I claim:

1. A new and distinct variety of Spathiphyllum plant, substantially as herein disclosed, characterized as to novelty by compact plant form with a larger ratio of bract to the whole plant as well as of bract to leaf in length, dark green colored leaves and round, big, erect and yellowish white colored bracts.

* * * * *